United States Patent [19]

Stein et al.

[11] 4,009,213
[45] Feb. 22, 1977

[54] CONTINUOUS PROCESS FOR THE SEPARATION OF MIXTURES OF FATTY SUBSTANCES OF DIFFERENT MELTING POINTS

[75] Inventors: Werner Stein, Erkrath-Unterbach; Helmut Hartmann, Langenfeld, both of Germany

[73] Assignee: Henkel & Cie G.m.b.H., Dusseldorf-Holthausen, Germany

[22] Filed: Mar. 9, 1976

[21] Appl. No.: 600,215

Related U.S. Application Data

[60] Continuation-in-part of Ser. No. 521,915, Nov. 7, 1974, Pat. No. 3,953,485, which is a division of Ser. No. 300,895, Oct. 26, 1972, Pat. No. 3,870,735.

[30] Foreign Application Priority Data

Nov. 11, 1971 Germany .................... 2155988

[52] U.S. Cl. .................................... 260/643 D
[51] Int. Cl.² ................................. C07C 29/24
[58] Field of Search ......................... 260/643 D

[56] References Cited

UNITED STATES PATENTS

| 2,530,042 | 11/1950 | Blimoff ................. | 260/643 D |
| 2,972,636 | 2/1961 | Hartmann et al. ......... | 260/643 A |

FOREIGN PATENTS OR APPLICATIONS

| 698,217 | 10/1953 | United Kingdom ......... | 260/643 A |
| 964,649 | 7/1964 | United Kingdom ......... | 260/643 A |

Primary Examiner—Joseph E. Evans
Attorney, Agent, or Firm—Hammond & Littell

[57] ABSTRACT

The invention relates to an improvement of the known continuous process for the separation of mixtures of fatty alcohols of different melting points, in which the starting mixture by treating with an aqueous wetting agent solution is converted to a dispersion of liquid fatty substances and solid fatty substance particles, the formed dispersion is separated into two phases of different specific gravities, the lighter phase consists substantially of the liquid fatty fraction and the heavier phase of a dispersion of the solid fatty particles in the aqueous wetting agent solution. After separation of this suspension the wetting agent solution is returned to the process. The improvement consists in withdrawing a part of the recycling wetting agent solution from said dispersion of fatty particles in the aqueous wetting agent solution by separation of some or all the aqueous solution from the solid fatty particles, the solid fatty particles with the remaining aqueous phase and adhering wetting agent are melted in the presence of an aqueous phase and the molten fatty fraction containing little wetting agent, is separated from the aqueous phase enriched with wetting agent which is recycled and the amount of wetting agent solution withdrawn is replaced with fresh wetting agent solution.

8 Claims, 2 Drawing Figures

CONTINUOUS PROCESS FOR THE SEPARATION OF MIXTURES OF FATTY SUBSTANCES OF DIFFERENT MELTING POINTS

This application is a continuation-in-part of our copending application Ser. No. 521,915, filed Nov. 7, 1974, now U.S. Pat. No. 3,953,485 which, in turn, was a division of application Ser. No. 300,895, filed Oct. 26, 1972, now U.S. Pat. No. 3,870,735.

THE PRIOR ART

German Pat. No. 977,544 discloses a process for the separation of mixtures of fatty acid esters, especially of triglyceride mixtures, into components of different melting points. This process involves preparing a dispersion of liquid fatty esters and separated solid fatty ester particles in an aqueous solution containing wetting agents and, optionally, non-surface-active electrolytes, and separating this dispersion into two phases of different specific gravities of which one consists substantially of the liquid fatty acid esters and the other of a suspension of the solid fatty acid esters in the aqueous wetting agent solution. Solid jacket centrifuges have proved satisfactory for this step in the process. The solid fatty ester particles and the aqueous wetting agent solution are then separated in a known manner, e.g., by filtration or by melting of the, until then, solid fatty acid esters, so that the latter as a continuous liquid phase can be separated from the aqueous phase. The aqueous wetting agent solution, free of fatty acid esters, is then recycled in the process.

U.S. Pat. No. 2,800,493 discloses, in addition to this process for the separation of mixtures of fatty acid esters, also a corresponding process for the separation of fatty acid mixtures into ingredients of different melting points. U.S. Pat. No. 2,972,636 describes the application of this process to mixtures of fatty alcohols. This separation principle has become known under the name "Hydrophilization Process".

Improvements in this "Hydrophilization Process" are described in copending, commonly-assigned U.S. patent application Ser. No. 102,471, filed Dec. 29, 1970, now U.S. Pat. No. 3,737,444, and Ser. No. 102,712, filed Dec. 30, 1970, now U.S. Pat. No. 3,733,343. According to these disclosures, a part of the wetting agent solution circulated during the separation of fatty acid or fatty acid ester mixtures into components of different melting point by means of the "Hydrophilization Process" is withdrawn and replaced by fresh water, fresh electrolyte solution or fresh aqueous wetting agent solution in order to maintain the wetting agent concentration essentially constant at the first separation step. This process is of special importance in the treatment of fatty acid mixtures which contain 0.8% to 15% by weight, preferably 1% to 10% by weight of non-fatty acid organic impurities.

The term "non-fatty acid organic impurities" (in short "NF") is to be understood to be organic substances which are derived from the raw material serving for the preparation of the mixtures of fatty acids or from the processing of the mixtures of fatty acids, to be separated. These organic substances are those whose compostion does not correspond to the formula R—COOH where R is a hydrocarbon containing 7 to 27, preferably 9 to 21 carbon atoms, straight or branched aliphatic, optionally cycloaliphatic, saturated or unsaturated. Such NF contents are found especially in undistilled fatty acids from a cleavage of the corresponding fat.

Under "organic impurities" or "NF" in the sense of the above definition are to be understood, among others, the substances occurring in natural fats, which in the cleavage or saponification of these fats do not furnish fatty acids but remain in the fatty acid mixtures. In addition, in fatty acids of synthetic origin, the "organic impurities" include the unreacted starting materials for the preparation of these fatty acids, such as paraffins, olefins, alcohols, aldehydes, etc., which after the optional working up of the crude fatty acids, remain partially or completely in the products of the process. These "organic impurities" may be acidic, ester-like or unsaponified products, such as hydroxyfatty acids, fatty acids peroxides, fatty acid hydroperoxides, dicarboxylic acids (such as dimeric fatty acids) partial glycerides, fatty acid or hydroxyfatty acid esters of hydroxyfatty acids, alcohols, aldehydes, ketones, phosphatides, sterols, carotinoids, tocopherol, gossypol and other phenolic components, hydrocarbons, as well as decomposition products of the above-mentioned substances. Some of these "organic impurities" may be separated from the fatty acids by distillation. Others have about the same boiling range as the fatty acids so that a purification of the fatty acid mixtures by distillation only is not always possible. The amount of these impurities can be determined by known analytical procedures. To be sure, the decision if a certain starting material has to be processed according to the process of the invention, does not always require the preceding analytical determination of all these above-mentioned "NF" components. It is mostly sufficient for the practice of the invention to determine the amounts of non-saponifiable material (US) and the amounts of partial or tri-glycerides. If the sum of these two "NF" components does not greatly exceed the above minimum amounts, the determination of the other "NF" components is not required.

It has already been suggested to add organic solvents to the fatty acid mixture to be separated with the acid of the hydrophilization process, in order to attain in this way, in the crystallization of the solid ingredients, an improvement of the separation effect. These organic solvents are in the spirit of the invention not to be considered as impurities derived from the preparation or the processing of the fatty acids.

The withdrawal from the recycling of wetting agent solution improves the separating effect not only for fatty acid mixtures, but also in the case of other fatty mixtures, especially when these fatty mixtures contain impurities which adversely affect the dispersion and therefore the separation result.

Provided the fractions of fatty substances obtained in the hydrophilization process are not chemically homogenous compounds, but are present as mixtures of components with different melting points, these fractions can be separated again in one or more further separation stages in the described manner. Thus, for example, the liquid phase obtained could be cooled further to a temperature at which the higher melting components separate in crystalline form, and from this mixture, after dispersion in wetting agent solution, the higher and lower melting fractions could again be isolated in the described way. It is thereby possible, but by no means necessary, to withdraw wetting agent solution in each stage of separation and replace by fresh agueous phase. It is often sufficient to remove wetting agent solution only in one stage of separation. However, by these processes, even if the separation can be improved by withdrawing wetting agent solution, a loss of wetting agent must be taken into account.

OBJECTS OF THE INVENTION

An object of the present invention is the development of an improvement in the "Rewetting or Hydrophilization Process" whereby better separation of the higher and lower melting point mixtures of fatty components are obtained continuously over long periods of time.

Another object of the present invention is the development of a continuous process for the separation of mixtures of fatty alcohols into fatty alcohol mixtures of different melting points by the steps of continuously dispersing said mixture of fatty alcohols consisting of an oily phase and a solid phase in a recycling aqueous wetting agent solution at a temperature whereby a dispersion of liquid and solid fatty alcohol particles is obtained, continuously separating said dispersion into two phases of different specific gravities, a lighter phase consisting substantially of liquid fatty alcohol fractions and a heavier phase consisting substantially of solid fatty alcohol particles dispersed in said aqueous wetting agent solution, continuously withdrawing said liquid fatty alcohol fractions, continuously separating said solid fatty alcohol particles from some or all of said aqueous wetting agent solution, continuously withdrawing said separated aqueous wetting agent solution, continuously melting said solid fatty alcohol particles with the remaining aqueous phase and adhering wetting agent, in an aqueous phase, continuously separating said melted fatty alcohol particles containing little wetting agent from an aqueous phase enriched with wetting agent, continuously withdrawing said melted fatty alcohol particles, continuously recycling said aqueous phase enriched with wetting agent to said dispersing step and continuously replacing said withdrawn part of said recycling aqueous wetting agent solution with a fresh aqueous solution whereby the concentration of said recycling aqueous wetting agent solution is maintained substantially constant at said dispersing step.

These and other objects of the present invention will become more apparent as the description thereof proceeds.

THE DRAWINGS

DESCRIPTION OF THE INVENTION

Figure 1:
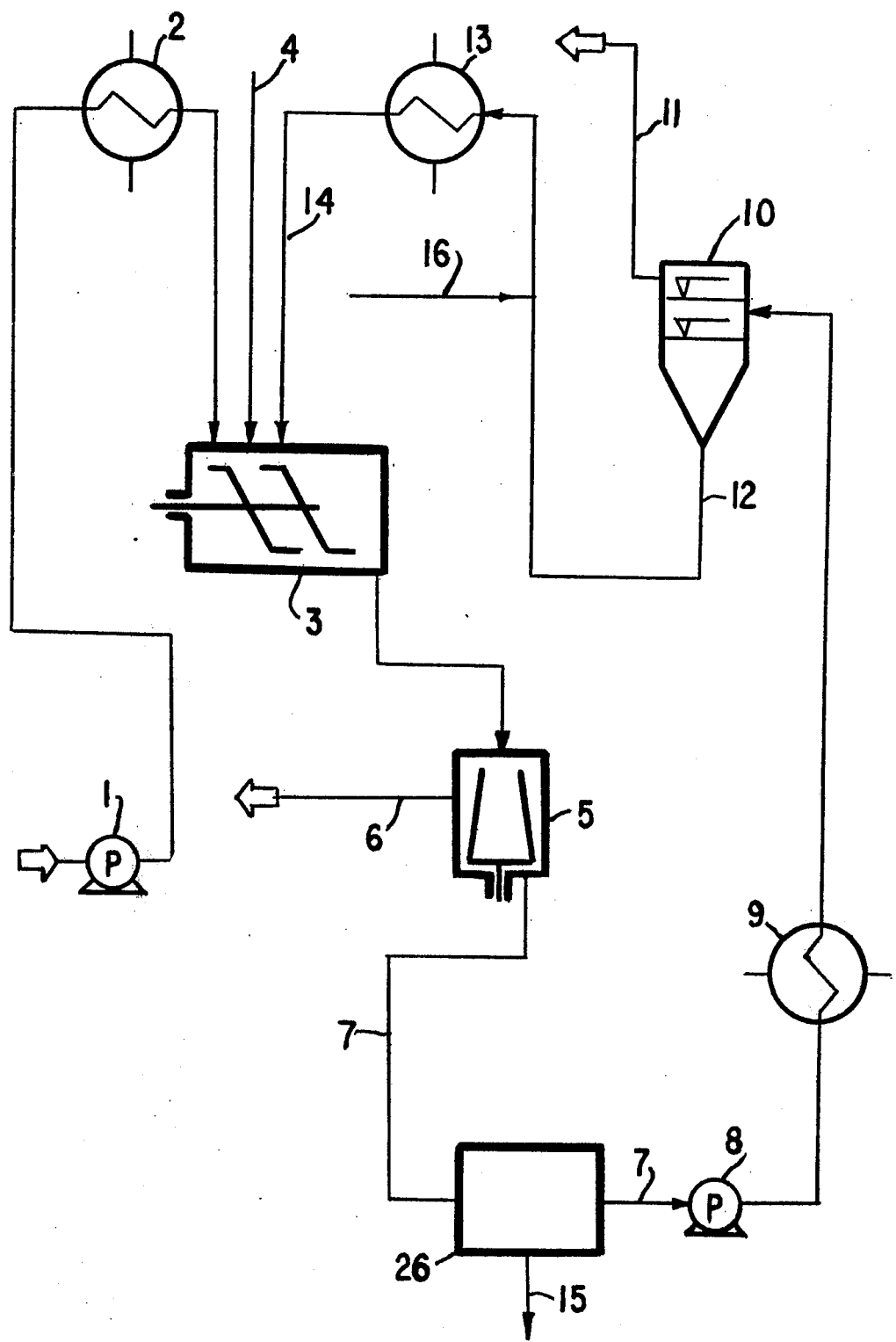
FIG. 1 is a flow diagram of the process of the invention.

The above objects have been achieved by an improved process for the separation of fatty mixtures into components of different melting point by converting the fatty mixtures into a dispersion of liquid and solid particles, separated from one another, of the fatty mixture in aqueous wetting agent solution, separation of this dispersion into two phases of different specific gravities, the lighter of which consists substantially of the liquid fat fractions and the heavier consists of a suspension of the solid fat particles in aqueous wetting agent solution, isolation of the solid fat fractions from the aqueous wetting agent solution, when at least a part of the aqueous wetting agent solution is withdrawn and replaced by water or by aqueous solution containing wetting agent and/or electrolyte, and the wetting agent which is not removed is returned to the process.

The process according to the invention is characterized in that the amount of wetting agent solution is removed from the said suspension, the solid fat particles are melted in the presence of the aqueous phase, the thereby formed, molten fat fraction reduced in wetting agent is separated from the aqueous phase enriched with wetting agent and the latter is returned to the process.

The particular advantage of this variation of the process lies in a reduction of the losses of wetting agent which previously occurred. The amounts of wetting agent contained in the solid fats are withdrawn when the solid fatty particles are separated during the cycle of the process, and the loss of wetting agent thereby caused would have to be compensated by addition of wetting agent. Surprisingly, small amounts of water are always sufficient to take up within the short time during the melting of the solid fatty particles the amounts of wetting agent contained therein. The aqueous wetting agent solution thereby resulting is of a concentration such that it can profitably be taken back into the process. Owing to this, the losses of wetting agent fall considerably.

The fatty mixtures to be treated according to the invention include a wide variety of fatty acid esters of vegetable, animal or synthetic origin.

Examples of the fatty acid esters of vegetable origin are coconut fat or palm kernel fat, palm oil, cottonseed oil, olive oil, soybean oil, peanut oil, linseed oil, rapeseed oil, caster oil, etc. Mixed fatty acid esters of animal origin are, for example, butter fat, chicken fat or goose fat, lard, mutton tallow or beef tallow, suet and bone fats, and also a large number of various fish fats and oils, train oil, blubber, whale oil, as for example menhaden oil, herring oil or sperm oil, cod liver oil, etc. These fatty acid ester mixtures of natural origin are mostly triglycerides, but the invention is not limited to the separation of triglycerides; thus for example, sperm oil contains in addition to triglycerides also fatty alcohol-fatty acid-esters. The fatty acid esters of other alcohols are also useful as starting mixtures.

Besides the native triglycerides, further processed products of natural fats can be separated, as for example, partly or completely hydrogenated fats, interesterification products of natural fats or esterification products of fatty acids and alcohols, as well as, very generally, derivatives of fatty acids and/or fatty alcohols of natural or synthetic origin.

Furthermore, fatty acid mixtures are utilizable as starting materials to be processed according to the invention which, for example, are obtainable by cleaving or by saponifying and acidifying fatty acid esters to the free fatty acids, especially from the fats occurring in nature. The separation of the fatty acid mixtures obtainable from the various kinds of tallow into commercial stearic acid (sometimes called stearin) and commercial oleic acid (sometimes called olein) are of special practical importance. But synthetically prepared fatty acids also can be treated according to the invention.

Finally, mixtures of fatty alcohols may be separated which are obtainable by hydrogenation of fatty acids or fatty acid esters, while these fatty acids may be derived, for example, from the above-mentioned natural fats. Fatty alcohols prepared from synthetic fatty acids or their esters or directly occurring fatty alcohols of synthetic origin, however, can also be treated as starting materials. In addition, fatty alcohols with straight chains can be separated from fatty alcohols of branched-chain, which have different melting points.

The fatty residues present in the starting mixtures to be treated according to the invention in the form of fatty acids or fatty alcohols preferably contain 6 to 26, especially 8 to 20 carbon atoms. When present as esters, the fatty acid or fatty alcohol components preferably contain the above amount of carbon atoms. According to the invention, compounds with branched chain fatty residues as well as resin or naphthenic acids, their esters and corresponding alcohols also come under the term "fatty substances".

As a matter of simplification, in the following specification the mixture to be separated, of fatty components of different melting points is called "starting material", the liquid phase obtained in the separation is called "oil", the solid phase obtained in the separation is called "solid ingredients". The term "solid ingredients" is used for higher melting fatty particles even when they are present under the then prevailing process conditions in a liquid state. The dispersion of solid and liquid fatty particles, to be separated from one another, in an aqueous wetting agent solution is denoted as "dispersion" for the sake of simplicity and the suspension of solid fat particles in aqueous wetting agent solution coming from the centrifuge is denoted as "suspension".

For the preparation of the dispersion of separated particles of solid fractions and oil, in aqueous wetting agent solution, a pasty mixture of crystalline solid fractions and oil is utilized. The separation obtainable according to the process is dependent, among other things, on the quality of the solid crystals. In order to obtain a good separation, it is advisable to completely melt the starting mixture and then to gradually cool it to the temperature at which the separation is to be effected. Scraper coolers have proved suitable for cooling the molten starting mixture. These consist of tubes with a cooling jacket, whose inner surface is kept free from the crystallizing solid fractions by rotating doctor blades. According to the crystallizing behavior of the starting mixture, this can leave the scraper cooler in a more or less strongly supercooled liquid state. It is, therefore, advisable to give the supercooled liquid starting mixture more time for crystallization of the higher melting solid ingredients before its further treatment.

The molten starting mixture, however, may also be cooled in another way to the separating temperature, for example, by mixing it with water or with aqueous wetting agent solution, and producing cold by evaporation of the water under reduced pressure. It is also possible to bring a starting mixture which has been precooled in the scraper cooler or by evaporation cooling, but is not yet at separation temperature to the separation temperature, by mixing with a colder aqueous phase.

The wetting agent solution serving for the dispersion of the starting mixture cooled to the separating temperature frequently has the same temperature as the mixture to be separated. The amount of the wetting agent solution should be about 0.5 to 3, preferably 1 to 2 parts by weight per part of the starting mixture to be separated present in the dispersion.

In addition to soaps, anionic, cationic, or nonionic water-soluble compounds which lower the surface tension of the aqueous solutions are utilizable. A removal of the liquid ingredients of the starting mixture from the surface of the solid ingredients occurs with the aid of the aqueous wetting agent solution. The following compounds which contain an alkyl radical with 8 to 18, preferably 10 to 16 carbon atoms in the molecule are useable, in addition to soap, as wetting agents: alkylbenzene sulfonates, alkylsulfonates, fatty alcohol sulfates, sulfated reaction products of fatty alcohols adducted with 1 to 10, preferably 2 to 5, mols of ethylene oxide and/or propylene oxide, monoglyceride sulfates, etc. The anionic wetting agents named are preferably used in the form of their sodium salts; but they can also be used in the form of their other alkali metal, ammonium and lower alkylolamine salts, such as potassium, ammonium, mono-, di- or triethanolammonium salts. The water-soluble adducts of ethylene oxide to alkylphenols or fatty alcohols are useable as nonionic compounds. The cationic surface-active compounds are primarily quaternary ammonium compounds with one aliphatic chain of 8 to 24 carbon atoms and three lower alkyl or lower alkylol chains, such as dodecyl-trimethyl-ammonium chloride. The use of the cationic compounds is preferred in the separation of fatty alcohols of different melting points.

Approximately, such amounts of wetting agents are used that in the dispersion formed, immediately prior to the entry in the separation centrifuge, 0.05 to 2, preferably 0.1 to 1, parts by weight of wetting agent per 100 parts by weight of aqueous solution are present. The above amounts for the wetting agents include not only the wetting agents actually dissolved in the aqueous phase, but also the amounts of wetting agent dissolved in the oil or adsorbed on the surface of the solid ingredients.

The effect of the aqueous wetting agent solution is improved if it contains dissolved non-surface-active electrolytes, inert to the starting mixtures. To this belong, e.g., the water-soluble chlorides, sulfates, or nitrates of mono- to trivalent metals, particularly of the alkali, alkaline earth and earth metals. Above all, additions of sodium sulfate and magnesium sulfate have proven desirable. The electrolyte concentration of the dispersion to be separated, lies in the range of 0.1% to 10%, preferably 1% to 5%, by weight. These numerical data, as also above in the case of the wetting agent concentration, are calculated on the total amount of electrolytes present in the dispersion based, however, on the aqueous phase present in the dispersion. In connection with the invention, by aqueous wetting agent solution, preferably a wetting agent solution containing electrolytes is meant.

In the mixing of the cooled starting mixture with the wetting agent solution, the oil is displaced from the surfaces of the solid ingredients, independently of whether the wetting agent solution is mixed with the starting mixture cooled to the separation temperature or whether the liquid starting mixture together with the wetting agent solution is brought to the separation temperature, so that the solid fractions are formed in the presence of the wetting agent solution. It has been found appropriate to combine the cooled starting mixture first with only a partial amount of a correspondingly more concentrated wetting agent solution, and to bring the so-formed more concentrated aqueous wetting agent solution gradually by addition of water, electrolyte solution, or correspondingly more dilute wetting agent solution to the desired final concentration. Advantageously, the cooled starting mixture is first combined with 5% to 50%, preferably 10% to 30%, of the total wetting agent solution to be used, and gradually so much of further solution is added that the desired final concentration is attained.

The dispersion is then separated into two phases of different specific gravity. Solid jacket centrifuges have proved specially advantageous for this purpose, and a number of different designs may be used, such as, for example, tube centrifuges, disk centrifuges, or continuous scaling centrifuges.

Of the phases thereby produced, the lighter or oil phase consists substantially of the liquid components of the starting mixture, and the heavier phase represents a suspension of the solids in aqueous wetting agent solution.

The wetting agent solution is now partly or completely removed from this suspension according to the invention. By "complete removal" of the wetting agent solution is meant an operation in which the wetting agent solution is separated until only amounts of liquid mechanically adhering to the solids are left, so that the solids are no longer obtained in a flowable state, but are obtained for example as a wet filter residue. Then an aqueous phase, for example, water or electrolyte solution, is added in such amount that the solids again become flowable and may be added as a liquid to the next stage of the process. The flowable aqueous slurry of the solids suitably contains 30% to 90% by weight, preferably 40% to 70% by weight of aqueous phase.

For the complete or partial separation of the wetting agent solution from the suspension, filters, screen, centrifuges, settling tanks, solid jacket centrifuges, hydrocyclones, centrifugal mud-separators and centrifugal concentrators are suitable. In the preferred method of operation only about 10% to 70%, preferably 15% to 50% of the wetting agent solution is removed, this amount being advantageously chosen as a function of the amount of water present in the dispersion so that the solids are obtained as a still flowable concentrate. The wetting agent solution can be removed continuously or portionwise from the suspension.

The remaining, still wet, solids preferably present as a flowable concentrate are now heated to melt the solids. Two liquid phases are formed which are separated from one another in known way, for example, by separators or centrifuges. The aqueous phase thus obtained contains in solution a large part of the wetting agent contained in the solid fractions, and it is returned to the process. In this way, the wetting agent solution removed from the suspension can be replaced by fresh solution with a minimum loss of wetting agent. If necessary, the solids may be again washed with water in order to remove therefrom the last traces of wetting agent.

The process according to the invention is frequently carried out in several stages, in which one or both of the fractions obtained in the first separation stage is, or are, converted again into a dispersion of solid and liquid fatty components, separated from one another, of correspondingly higher or correspondingly lower temperature, and these are again separated. The process according to the invention can also be used for these further separation stages. When the solids obtained as intermediate fractions are returned to the process, it is often sufficient to restrict the use of the variant of the process of the invention to those end stages in which the solids are removed from the process as end products.

In FIG. 1, a flow diagram suitable for the execution of the separation process, according to the invention, is illustrated. The melting starting mixture, to be separated, is conducted through the feed pump 1 to the scraping condenser 2, and leaves it as a pasty mixture of oil and solid ingredients. This mixture passes into the mixer 3 which, advantageously, consist of several mixing chambers connected in series, each of which is provided with a stirrer. In the first mixing chamber, the cooled starting material is stirred up with the more concentrated wetting agent solution, flowing in through the line 4, to give a dispersion. In the successive mixing chambers, the more dilute wetting agent or electrolyte solution is intermixed. Thereby, a dispersion is formed in which the oil particles and the particles of the solid ingredients are separately dispersed in the wetting agent solution. In order to convert the pasty starting mixture into a dispersion in aqueous wetting agent solution, however, other mixing devices are also suitable. It is sometimes sufficient to expose the materials to be mixed to a turbulent flow.

This dispersion from the mixer 3 is then separated with the aid of a solid-jacket centrifuge 5 into an oil as the lighter phase and a dispersion of the solid particles in the wetting agent solution as the heavier phase. The oily lighter phase is withdrawn by line 6. The heavier phase is conducted through line 7, according to the invention to the concentrator 26 where a part of the wetting agent solution is removed and is discharged through line 15.

The feed pump 8 carries the remaining concentrated suspension of the solids, possibly after addition of fresh aqueous phase, to the heater 9 where the suspension is heated to melt the solid ingredients. The wetting agent adhering to the solid fractions goes over into the aqueous phase. The molten solid ingredients and the wetting agent solution move then together to the separator 10 from which the molten solid ingredients leave at line 11 as the lighter phase and the wetting agent solution leaves at line 12 as the heavier phase. This heavier aqueous phase containing the recovered wetting agent from the solid fraction is recycled through the heat exchanger 13, through the line 14 to the mixer 3.

In contrast to the methods of operation described in the examples of the above-mentioned earlier applications, the wetting agent solution withdrawn according to the present invention, is thus removed before the solids are melted. The wetting agent solution may be removed continuously or portionwise from time to time as required.

If the amount of aqueous phase removed in the concentrator 26 before the melting of the solids is not, or not completely, replaced by fresh aqueous phase, a corresponding amount of fresh aqueous phase may be added through line 16. It is, however, not absolutely necessary to introduce the fresh solution where in FIG. 1, the line 16 discharges into the line 12 coming from the separator 10. Naturally, the fresh solution can be charged directly as wetting agent or electrolyte solution into the mixer 3, particularly into the successively arranged mixing chambers designed for the dilution of the first formed dispersion.

According to a further embodiment of the invention, each of the two obtained fatty fractions, the lower melting (oil) and/or the higher melting (solid ingredients) can be converted to a dispersion of separated solid fatty particles and liquid oil in aqueous wetting agent solution, and from this a lower melting and a higher melting fatty fraction can be isolated. In addition, in these final separation stages, this variant of the process according to the invention can be conductive to a more complete recovery of the wetting agent.

If the oil, obtained in a preceding separation, is processed according to the invention procedure, it is cooled by one of the above-described methods, i.e., in the absence or also the presence of aqueous wetting agent solution, in comparison to the first separation step, to a suitably lower separation step, to a suitably lower separation temperature (cold step). The wetting agent solution circulating in the second separation step can form its own wetting agent solution cycle separated from that of the first separation step. The wetting agent solution may, however, also flow through both separation steps.

If the process is applied at correspondingly higher temperatures to the solid ingredients obtained in a preceding separation step (warm step), it can be carried out according to two process variants. The one variant consists in heating the wetting agent solution with the dispersed solid ingredients in it so that a part of the solid ingredients melts and now forms an oil in this dispersion. The second variant consists in completely melting the solid ingredients and to convert them again, as described above, to a dispersion of separated particles of oil and solid particles, from which the oil and the solid ingredients are isolated, however, at a higher temperature than was the case in the first separation step.

Figure 2:
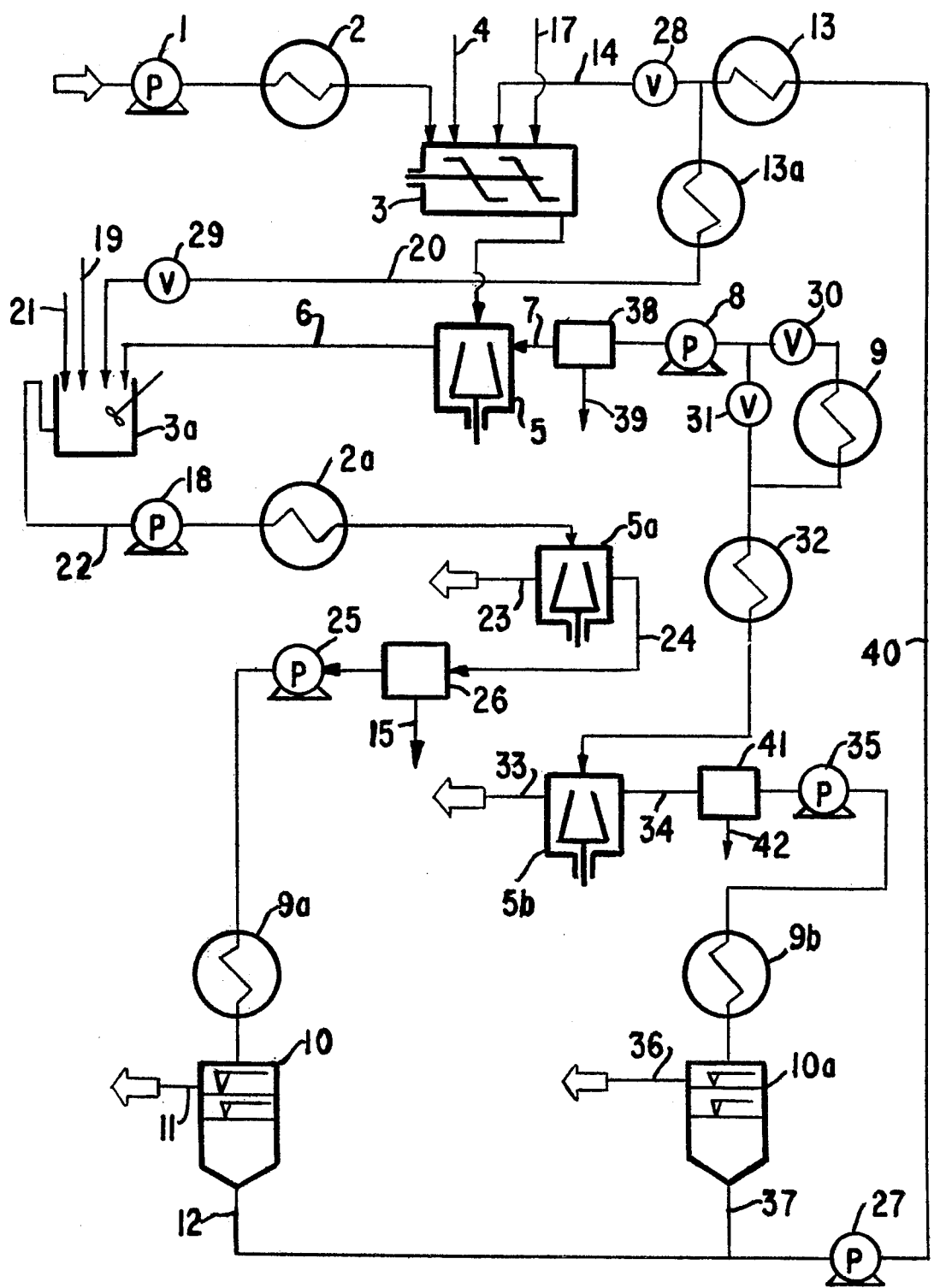
FIG. 2 is a flow diagram of another embodiment of the process of the invention.

In FIG. 2 a flow diagram for the renewed separation, at higher and lower temperature, of both fractions obtained in the first separation step is illustrated. The starting mixture, to be separated, is pumped by the pump 1 through the scraping condenser 2 into the mixer 3. This is preferably constructed in the manner described above. It consists of single mixing chambers through which the starting mixture is successively passed. In the first mixing chamber, the starting mixture leaving the cooling and crystallizing scraping condenser 2 is first combined with more concentrated wetting agent solution through line 4. Water free of wetting agent, or electrolyte solution free of wetting agent, can be added through line 17, and wetting agent solution recovered from the solid fractions and recycled, is added through line 14. The dispersion formed in the mixer 3 flows into the centrifuge 5 and is there separated into two phases. The heavier phase, present as a suspension of solid ingredients in aqueous wetting agent solution is discharged through the line 7 into the concentrator 38. The separated part of the aqueous phase is removed at line 39. The remaining more concentrated suspension runs into the pump 8, while the lighter phase consisting substantially of oil is discharged through the line 6 for further treatment.

For the separation of small amounts of higher melting ingredients (cold step) still present in this oil, it is conducted through the line 6 into the mixer 3a. The latter may only consist of a simple mixing vessel. In the mixer 3a, the oil is admixed with the wetting agent solution, returned from the process through line 20. If desired, through the lines 19 or 21 more concentrated wetting agent solution and/or water, free of wetting agent, or electrolyte solution, free of wetting agent, may be applied. The aqueous solutions added at this point may have lower temperatures than the oil. For this purpose, the recycling aqueous wetting agent solution can be cooled through the heat exchanger 13a. The amount of this aqueous wetting agent solution is measured out by the valve 29.

The dispersion formed in the mixer 3a, in which certain amounts of crystallized solid ingredients may already be present, is passed through the line 22 and the pump 18 into the scraping condenser 2a where it is cooled to the separation temperature. From there it is passed to the centrifuge 5a from which an oil is withdrawn at line 23 as the lighter phase whose turbidity point is lower than the turbidity point of the oil leaving the centrifuge 5. At line 24, a suspension of solid ingredients in aqueous wetting agent solution is obtained as the heavier phase which is separated in the concentrator 26, and a part of the aqueous phase is withdrawn through line 15. The pump 25 conveys the concentrated suspension to the heater 9a which it leaves as a mixture of aqueous wetting agent solution and molten solid ingredients. In the separator 10 this mixture is separated into the molten solid ingredient withdrawn at line 11 and the aqueous wetting agent solution withdrawn at line 12. A substantial part of the wetting agent adhering to the solid fraction is present in this aqueous wetting agent solution.

There are two possibilities for the processing at elevated temperatures (warm step) of the suspension of solid ingredients in aqueous wetting agent solution leaving the centrifuge 5: (a) either the total dispersion is heated to a temperature where a part of the solid ingredients melts, or (b) the suspension is heated to the complete melting of the solid ingredients and then cooled to the separating temperature of the warm step. In the first case, the pump 8 feeds the suspension, with valve 30 closed, through the open valve 31 to a combination heating and cooling apparatus 32, which is heated in this case and from which then a dispersion of oil and separated solid particles in aqueous wetting agent solution leaves. In the second case, the pump 8 feeds the suspension, with the valve 31 closed, through the open valve 30 to the heat exchanger 9 where the solid ingredients are completely melted. The emerging mixture is converted in the successively connected combination heating and cooling and crystallizing apparatus 32 to a dispersion of separated particles of oil and solid ingredients in aqueous wetting agent solution. Either of these dispersions are separated in the centrifuge 5b into the oil, withdrawn as the lighter phase at line 33, and the suspension of solid ingredients in aqueous wetting agent solution, withdrawn as the heavier phase at line 34.

The suspension emerging at line 34 is concentrated in the concentrator 41 by withdrawal of a part of the wetting agent solution emerging at line 42. The pump 35 feeds this concentrated suspension into the heater 9b. The mixture of wetting agent solution and molten solid ingredients formed is separated in the separator 10a into the molten solid ingredients withdrawn at line 36 and into the aqueous wetting agent solution. The latter is withdrawn at line 37.

The part of the warm concentrated wetting agent solution leaving the separators 10 and 10a not withdrawn from circulation through lines 15 and 42, is returned together to the process through the pump 27 and the line 40, and is cooled by passage through the heat exchanger 13 to the temperature at which it shall enter into the first step. The valves 28 and 29 control the partial amounts of recycling aqueous wetting agent solution which are returned to the first or the cold step.

By the process scheme, according to FIG. 2, four fractions of different melting points or turbidity points are obtained. If tallow fatty acids are separated in this manner into stearin and olein, the olein recovered from the cold step and the stearin recovered from the warm step are the proper products of the process. The two other fractions of fatty acids are returned to the starting material to be processed in the first separation step.

The following examples are illustrative of the process of the invention without being deemed limitative in any respect.

EXAMPLES

The fatty acids, the treatment of which is described in some Examples, were prepared from triglycerides by cleaving with water at elevated temperatures and increased pressure and then separating the aqueous glycerine-containing phase. "Distillate fatty acids" refer to distillates of these fatty acids as cleaved from triglycerides.

In Examples 1 to 6, starting materials were processed according to the flow diagram of FIG. 1. The molten starting mixture was passed through the pump 1 to the scraper cooler 2 and left this as a slurry of oil and solid fractions. This slurry went to the mixer 3 consisting of several mixing chambers in series, each provided with a stirrer. In the first mixing chamber the cooled starting material was stirred with the wetting agent concentrate flowing through line 4 to give a dispersion. The following mixing chambers served for the dilution with wetting agent solution or electrolyte solution. Provided it is not expressly stated otherwise, these solutions had the same temperature as the slurry of oil and solids emerging from the scraper cooler 2. In the mixer 3 the dispersion was formed, in which the oil particles and the solid fraction particles, separated from one another, were present dispersed in the wetting agent solution (the data contained in the examples on the wetting agent and/or electrolyte contents also applies to this dispersion. It includes the total amounts of wetting agent and/or electrolyte present therein, but related to the aqueous phase).

The solid jacket centrifuge 5 separated this dispersion into the lighter oil obtained at line 6 and the heavy suspension obtained at line 7. The latter was separated in the concentrator 26 (a centrifugal separator served for this purpose) into a concentrated suspension and a weak solution of wetting agent free from solid fractions. This solution was discarded through line 15. The concentrated suspension was passed by means of the pump 8 to the heater 9, where the suspension was heated until the solids melted. The wetting agent adhering to the solid fractions thereby went over for the most part into the residual aqueous phase. Molten solids and wetting agent solution then passed together to the separator 10, from which the molten solids emerged as the lighter phase at line 11, and the wetting agent solution as the heavier phase emerged at line 12. This heavier phase with the recovered wetting agent contained therein went through the heat exchanger 13 and the line 14 back into the mixer 3. The loss of liquid emerging at line 15 by the removal of wetting agent solution was compensated by addition of fresh aqueous phase at line 16.

It is not absolutely necessary to introduce the fresh solution at the place where in the drawing the line 16 feeds into line 12. The fresh solution can obviously also be fed directly into the mixer 3, especially into the final mixing vessels intended for the dilution of the first formed dispersion.

Although the higher melting fractions obtained are present in the molten state, they are for the sake of simplicity referred to as "solid fractions".

In the Examples the consumption of wetting agent in the process according to the invention is compared with the consumption of wetting agent in operation without withdrawing recycling wetting agent solution or with withdrawing of wetting agent solution after melting the separated solid fractions. The separation process without withdrawing a part of the recycling wetting agent solution is indeed known in principle, but the details of the conditions used in the process come from internal unpublished work. Therefore, these comparative examples are not to be regarded as the state of the art. In the method described for comparison relating to withdrawal of part of the wetting agent solution after melting the solid fractions the concentrator 26 was avoided by a conduit leading from the line 7 direct to the pump 8. The wetting agent solution was removed in line 12 by a discharge cock. The bypass conduit and the discharge cock are not shown in FIG. 1. This type of withdrawal of part of the recycling wetting agent solution is the object of the earlier U.S. patent applications Ser. Nos. 102,471 and 102,712.

The "NF" contents ("NF" = non-fatty acid-like components) indicated in the Examples of the fatty acid mixtures to be separated are the sums of the unsaponifiable contents and the glyceride contents. The latter are calculated from the analytically determined contents of ester-like bound glycerine with the calculated presumption that all glycerine is present as diglyceride (actually: mixture of mono-, di- and tri-glycerides) and that the fatty acids present in the glycerides have the same average molecular weight as the free fatty acids.

EXAMPLE 1 a. Treatment of distilled fatty acid cleaved from tallow (Acid No. = 204, Saponification No. = 206, Iodine No. = 52, NF = 1% by weight)

1. Conventional operation without withdrawal of wetting agent solution:

1 t/h (1000 kg/h) of this starting mixture was cooled in the scraping condenser to 5° C. The pasty mixture of oil and solid ingredients obtained was first admixed with 0.3 t/h of more concentrated and subsequently with 1.2 t/h of more dilute wetting agent solution, so that the dispersion leaving the mixer contained, per one part by weight of the cooled starting material, 1.5 part by weight of wetting agent solution. This wetting agent solution had a wetting agent content of 0.25% by weight of sodium decylsulfate and an electrolyte content of 1% by weight of $MgSO_4$. The dispersion was then separated into an oily and an aqueous phase. As oily phase, 0.39 t/h of olein with a turbidity point of 4° C were obtained. After process of the aqueous phase, 0.61 t/h of stearin with an I. No. = 28 were obtained. The aqueous wetting agent solution was totally recycled.

2. Conventional operation with withdrawal of part of the recycling wetting agent solution:

When the same fatty acid was treated in an analogous way, but with continuous withdrawal of 0.2 t/h of wetting agent solution from the cycle at a place (not shown) in the line 12 and replacement of the removed amount by the same amount of 1% $MgSO_4$ solution (at line 16) with at the same time introduction of an amount of more concentrated wetting agent solution (by line 4) such that the wetting agent content of the dispersion remained permanently at the calculated value, 0.52 t/h of stearin (I. No. = 17) and 0.48 t/h of olein (turbidity point 4° C) were obtained. Thus by the withdrawal of part of the recycling wetting agent solution and its replacement, a purer stearing and a higher yield of olein were obtained. Of course 2 kg of sodium dodecyclsulfate per t of withdrawn wetting agent solution were lost.

3. Operation according to the present invention:
But when 0.2 t/h of wetting agent solution were withdrawn from the cycle in the concentrator 26, i.e. from the cold suspension, the loss of wetting agent was reduced by 65% to 0.7 kg/t of withdrawn wetting agent solution.

b. Treatment of undistilled fatty acid cleaved from tallow (Acid No. = 199, Saponification No. = 206, I. No. = 53, NF = 4.5% by weight)

1. Conventional operation without withdrawal of wetting agent solution:
This starting material was treated essentially under the same conditions as described in Example 1a. The content of sodium decylsulfate in the dispersion was increased to 0.3% by weight. In spite of the increased wetting agent content, the separation results were unsatisfactory. After processing, 0.355 t/h of olein (turbidity point 4° C) and 0.645 t/h of stearin (I. No. = 31) were obtained.

2. Conventional operation with withdrawal of wetting agent solution:
On the other hand, in a way similar to that described in Example 1a (2) with the same constant content of sodium decylsulfate, 0.5 t/h of the wetting agent solution was removed from the cycle and replaced by 0.5 t/h of 1% $MgSO_4$ solution, then 0.46 t/h of olein (turbidity point 4° C) and 0.54 t/h of stearin (I. No. = 19) were obtained. However, 2.5 kg of sodium dodecylsulfate per $t$ of withdrawn wetting agent solution were lost.

3. Operation according to the invention:
But when, as described above, the 0.5 t/h of wetting agent solution was removed at line 15, i.e. from the cold stearin suspension, the loss of wetting agent was reduced by 68% to 0.8 kg/t of withdrawn wetting agent solution.

EXAMPLE 2 a. Treatment of distilled cottonseed oil fatty acids (Acid No. = 202, Saponification No. = 204, I. No. = 103, NF=1.7% by weight).

1. Conventional operation without withdrawal of wetting agent solution:
Starting material cooled to 5° C (separating temperature)
Dispersion formed from 1 t/h of cooled fatty acids 0.4 t/h of more concentrated wetting agent solution, diluted with 1.3 t/h of recycled wetting agent solution.
Composition of the wetting agent solution: 0.25% by weight of sodium decylsulfate and 2% by weight of $Na_2SO_4$.
Process products:
0.77 t/h of liquid fatty acids (turbidity point 6° C, I No. = 127)
0.23 t/h of solid fatty acids (I No. = 26)

2. Conventional operation with withdrawal of wetting agent solution:
Withdrawn wetting agent solution: 0.4 t/h replaced by $Na_2SO_4$ solution, with the content of wetting agent and $Na_2SO_4$ held constant.
Process products:
0.78 t/h of liquid fatty acids (turbidity point 6° C, I No. = 127)
0.22 t/h of solid fatty acids (I No. = 18)
Loss of wetting agent: 2.4 kg/t of withdrawn wetting agent solution.

3. Operation according to the invention:
The 0.4 t/h of wetting agent solution was removed by means of a hydrocyclone from the cold suspension. Owing to this the loss of wetting agent fell by 71% to 0.7 kg/t of withdrawn wetting agent solution.

b. Treatment of undistilled fatty acid cleaved from cottonseed oil (Acid No. = 197, Saponification No. = 204, I No. = 103, NF = 4.4% by weight).

1. Conventional operation without withdrawal of the wetting agent solutions:
Starting material cooled to 5° C (separating temperature)
Dispersion formed from 1 t/h of cooled fatty acids, 0.4 t/h of more concentrated wetting agent solution diluted with 1.5 t/h of recycled wetting agent solution.
Composition of the wetting agent solution: 0.45% by weight of sodium decylsulfate and 2.5% by weight of $Na_2 SO_4$.
Process products:
0.735 t/h of liquid fatty acids (turbidity point 3° C, I No. = 128)
0.265 t/h of solid fatty acids (I No. = 33)

2. Conventional operation with withdrawal of wetting agent solution:
Withdrawn wetting agent solution: 0.7 t/h replaced by $Na_2SO_4$ solution, with the content of wetting agent and $Na_2SO_4$ held constant.
Process products:
0.770 t/h of liquid fatty acids (turbidity point 3° C, I No. = 128) 0.230 t/h of solid fatty acids (I No. = 21).
Loss of wetting agent: 2.6 kg/t of withdrawn wetting agent solution.

3. Operation according to the invention:
When 0.7 t/h of wetting agent solution was removed by means of a centrifuge from the cold suspension, the loss of wetting agent fell by about 81% to 0.5 kg/t of withdrawn wetting agent solution.

EXAMPLE 3

Treatment of distilled fatty acid cleaved from fish oil (Acid No. = 199, Saponification No. = 201, I No. = 126, NF = 1.8% by weight)

1. Conventional operation without withdrawal of the wetting agent solution:
Starting mixture cooled at 5° C (separation temperature).
Dispersion formed from 1 t/h of cooled fatty acids, 0.5 t/h of more concentrated wetting agent solution diluted with 1.5 t/h of recycled wetting agent solution.
Composition of the wetting agent solution: 0.3 % by weight of sodium decylsulfate and 2% by weight of $MgSo_4$.
Process products:
0.795 t/h of liquid fatty acids (turbidity point 3° C, I No. = 152)
0.205 t/h of solid fatty acids (I No. = 34)

2. Conventional operation with withdrawal of the wetting agent solution:

Withdrawn wetting agent solution: 0.45 t/h replaced by MgSO$_4$ solution with the content of wetting agent and MgSO$_4$ held constant.

Process products:

0.81 t/h of liquid fatty acids (turbidity point 3° C, I No. = 151)

0.19 t/h of solid fatty acids (I No. = 23).

Loss of wetting agent: 2.2 kg/t of withdrawn wetting agent solution.

3. Operation according to the invention:

When 0.45 t/h of wetting agent solution were removed from the cold suspension the loss of wetting agent fell by about 68% to 0.7 kg/t of withdrawn wetting agent solution.

EXAMPLE 4

Treatment of distillation deacidified palm oil (Acid No. = 1.1, Saponification No. = 201, I No. = 49).

1. Conventional operation with withdrawal of the wetting agent solution:

Starting material cooled to 30° C (separation temperature)

Dispersion formed from 50 kg/h of cooled palm oil and 40 kg/h of wetting agent solution.

Composition of the wetting agent solution: 0.6% by weight of sodium dodecylsulfate and 5% by weight of Na$_2$SO$_4$.

Withdrawn wetting agent solution: 10 kg/h replaced by

Na$_2$SO$_4$ solution, with the content of wetting agent and Na$_2$SO$_4$ held constant.

Process products:

45.5 kg/h of oil (rising melting point 31° C, I No. = 53) 4.5 kg/h of solid fractions (rising melting point 52° C, I No. = 19.8)

Loss of wetting agent: 5.5 g/kg of withdrawn wetting agent solution.

2. Operation according to the invention:

When 10 kg/h of wetting agent solution were removed from the cold suspension, the loss of wetting agent fell by 93% to 0.4 g/kg of withdrawn wetting agent solution

EXAMPLE 5

1. Conventional operation with withdrawal of wetting agent solution:

Starting mixture: The lower melting fractions from palm oil (rising melting point 31° C, I No. = 53) obtained by the process of Example 4.

Starting material cooled to 20° C (separation temperature).

Dispersion formed from 50 kg/h of starting mixture and 50 kg/h of wetting agent solution.

Composition of the wetting agent solution: 0.55% by weight of sodium dodecylbenzenesulfonate, 5.0% by weight of Na$_2$SO$_4$.

Withdrawn wetting agent solution: 10 kg/h replaced by fresh wetting agent solution, with the content of wetting agent and MgSO$_4$ held constant.

Process products:

38 kg/h of an oil, liquid at 20° C (I No. = 58.5)

12 kg/h of solid fractions (I No. = 34, rising melting point 36° C) with largely cacoa butter-like properties.

Loss of wetting agent: 5.9 g/kg of withdrawn wetting agent solution.

2. Operation according to the invention:

When 10 kg/h of wetting agent solution were removed from the cold suspension, the wetting agent consumption fell by 98% to 0.1 g/kg of withdrawn wetting agent solution.

EXAMPLE 6

1. Conventional operation with withdrawal of the wetting agent solution:

Starting mixture: Palm kernel oil (Acid No. = 10.7, Saponification No. = 251, I No. = 17.7, rising melting point 28.1° C).

Dispersion formed from 50 kg/h of the pre-crystallized starting mixture at 24.5° C and 50 kg/h of wetting agent solution at 22° C; temperature of the dispersion (separating temperature) = 23.2° C.

Composition of the wetting agent solution: 0.5% by weight of the Na salt of a sulfated product of addition of 2.1 mol of propylene oxide to 1 mol of secondary alcohols with 14 to 15 carbon atoms, 5% by weight of Na$_2$SO$_4$.

Withdrawn wetting agent solution: 8 kg/h replaced by Na$_2$SO$_4$ solution, with the content of wetting agent and Na$_2$SO$_4$ held constant.

Process products:

35 kg/h of oil (Acid No. = 13.0, Saponification No. = 244, I No. = 22.5)

15 kg/h of solid fractions (Acid No. = 6.2, Saponification No. = 262, I No. = 7.8, rising melting point 32.4° C). Loss of wetting agent: 4.6 g/kg of withdrawn wetting agent solution.

Operation according to the invention:

When 8 kg/h of wetting agent solution were removed from the cold suspension, the loss of wetting agent fell by 93% to 0.3 g/kg of withdrawn wetting agent solution.

EXAMPLE 7

This example describes the processing of an undistilled fatty acid mixture (Acid No. = 204, Saponification No. = 207, I No. = 49, NF = 0.9%) obtained by the cleaving of beef tallow of technical quality, into olein and commercial stearin with use of an apparatus according to FIG. 2, whereby fractions obtained in the first separation step were separated in one successively arranged step each (warm step or cold step). Part of the wetting agent solution was withdrawn in each case. In the conventional operation this occurred after the hot or cold stage, i.e. the wetting agent solution was removed after melting the solid fractions downstream of the separators 10 and 10a by valves (not shown). The centrifuges 26, 38 and 41 operating as concentrators were avoided by lines which are not shown in FIG. 2 for reasons of good visibility. In the operation according to the invention part of the wetting agent solution was removed from the cold suspensions, which emerge from the centrifuges 5, 5a and 5b, by the concentrators 26, 38 and 41, the wetting agent solution emerging at lines 15, 39 and 42. The loss of wetting agent solution thereby occurring is compensated by addition of fresh aqueous phase.

Conventional operation with withdrawal of the wetting agent solution:

The starting mixture was cooled to 30° C with a throughput of 1 t/h in the scraping condenser 2 and admixed in the mixer 3 with 0.2 t/h of a 1% Na$_2$SO$_4$ solution at 28° C added at line 17, and 1.4 t/h of a 1% NaSO$_4$ solution at 29° C, recycled from the process, containing sodium dodecylsulfate added at line 14. In addition, such amounts of a 10% sodium dodecylsulfate solution were measured out and added at line 4, that the dispersion leaving the mixer 3 with a temperature of 29° C contained 0.19% by weight of sodium dodecylsulfate, based on the aqueous phase. From the centrifuge 5, 604 kg/h of olein (I No. = 74) and an aqueous dispersion of 396 kg/h of a commercial stearin (I No. = 11) were separated.

This dispersion was led through the warm step with the aid of the feeding pump 8, with the valve 30 closed, passed the valve 31 and through the scraping cooler 32, heated with hot water. A warm dispersion at 49.3° C of oil and solid ingredients was formed which was separated in the solid-jacket centrifuge 5b, maintained at 49° to 50° C. At line 33, 72 kg/h of a liquid fatty acid (I No. = 35) were obtained. The suspension of the solid ingredients in aqueous wetting agent solution was fed through the pump 35 to the heat exchanger 9b and then heated to 90° C. From the separator 10a at line 36, 324 kg/h of a commercial stearin (I No. = 6.1) were obtained.

The 604 kg/h of olein at 29° C, obtained in the first separation step, were admixed in the mixer 3a with 500 kg/h of recycled sodium dodecylsulfate solution containing 1% of $Na_2SO_4$ at a temperature of 16° C added at line 20, and with as much of 10% sodium dodecylsulfate solution added at line 21 that the sodium dodecylsulfate content of the formed dispersion, containing already certain amounts of solid ingredients, was 0.18% by weight, based on the aqueous phase. This dispersion was cooled in the scraping condenser 2a to 8° C, and separated in the solidjacket centrifuge 5a into 416 kg/h of olein (I No. = 90, turbidity point 6° C) and into an aqueous suspension of 188 kg/h of solid fatty acid (I No. = 38) in aqueous wetting agent solution.

The 416 kg/h of olein (I No. = 90) obtained in the cold step, and the 324 kg/h of commercial stearin (I No. = 6) obtained in the warm step, are considered as final products, the intermediate fractions (188 kg/h of fatty acids (I No. = 38) solid at 8° C, and the 72 kg/h of fatty acids (I No. = 35) liquid at 49° C, were combined and returned to the process.

Of the wetting agent solution recycling at about 1.6 t/h, after the separation of the molten solid fractions, about 0.6 t/h (37.5%) were withdrawn out and replaced.

The loss of wetting agent was 2.2 kg/t of withdrawn wetting agent solution.

Operation according to the invention:

When 0.6 t/h of withdrawn wetting agent solution were removed from the cold solid dispersions (0.2 t/h each at lines 15, 39 and 42) the loss of wetting agent fell in the remaining similar operation by 64% to 0.8 kg/t of withdrawn wetting agent solution.

EXAMPLE 8

The example describes the processing of a mixture of saturated and unsaturated fatty alcohols having a chain length of from 16 to 18 carbon atoms and an iodine number of 47 a. 300 parts of a molten mixture of saturated and unsaturated fatty alcohols having a chain length of from 16 to 18 carbon atoms and an iodine number of 47 was pumped continuously at a rate of 300 kg/h through a scraping condenser in which the fatty alcohols were cooled to 25° C and crystallized during a stay period of 2 hours. 450 kg/h of an aqueous solution which contained 0.6% dodecyl-trimethyl-ammonium chloride, as well as 10% $MgSO_4$ wre continuously added under stirring to the suspension of solid and liquid fatty alcohols thus formed. The resulting aqueous fatty alcohol dispersion was subsequently separated in a solid-jacket centrifuge into liquid fatty alcohols, on the one hand, and into an aqueous suspension of the solid fatty alcohols on the other hand.

25% of an aqueous solution without solid particles were separated from the suspension of the solid portions and discharged from the process. This permitted a trouble-free, continuous operation during the processing of crude fatty alcohols. The separate and discharge portions of the aqueous phase contained 0.07% of dodecyl-trimethyl-ammonium chloride. The remaining dispersion of the solid fatty alcohols contained in the aqueous phase 0.48% of dodecyl-trimethyl-ammonium chloride.

70.1% of solid fatty alcohols, iodine number 36.0 and 29.9% of liquid fatty alcohols, iodine number 70.3, were obtained.

b. In a process according to the state of the art, the aqueous solution was discharged with a content of wetting agents of 0.6%. Since the aqueous phase to be discharged in the process of the invention contained only 0.07% wetting agents, the resulting loss of wetting agents could be reduced to about 1/10.

EXAMPLE 9

The example describes the processing of a mixture of branched and straight chained saturated fatty alcohols having a chain length of from 16 to 19 carbon atoms and an iodine number 0.4.

a. 300kg/h of molten mixture of branched and straight chained Oxoalcohols having chain length of from 16 to 19 carbon atoms and an iodine number of 0.4, were pumped continuously, at a rate of 300kg/h through a scraping condenser, in which the fatty alcohols were cooled to 25.3° C while continuously being treated mechanically, and crystallized. 300kg/h of an aqueous solution which contained 0.6% tetradecyl-trimethyl-ammonium chloride and 9.5% $MGSO_4$ were continuously added with agitation to the resulting suspension of solid and liquid oxoalcohols thus formed. The resulting aqueous fatty alcohol dispersion formed was separated in a solid-jacket centrifuge into liquid fatty alcohols on the one hand and into an aqueous suspension of the solid fatty alcohols on the other hand.

From the aqueous suspension of the solid components, 15% of the aqueous solution without solid components were separated at 25° C, before the melting of the solid components, and discharged from the process cycle. Thereby, even when processing crude fatty alcohols, a smooth, continuous operation was made possible. The separated and discharged portions of the aqueous phase contained 0.08% of tetradecyl-trimethyl-ammonium chloride. The remaining aqueous dispersion of the solid components contained 0.58% of tetradecyl-trimethyl-ammonium chloride after melting.

83.5% liquid alcohols, melting point 22.0° C and 16.5% solid fatty alcohols, melting point 45.3° C were obtained.

b. In a procedure according to the prior art, it would have been necessary to discharge an aqueous solution with a wetting agent content of 0.6%. Since, with the procedure of the invention, the aqueous phase to be discharged contained only 0.08% wetting agent, the resulting reduction of the wetting agent loss was about 1/8.

EXAMPLE 10

If the experiment is carried out in the same manner as Example 9 (a), except that the cooling, crystallization and separation is done at 20.2° C, the wetting agent losses which resulted are in agreement with the figures of Example 9 (a). The following products, 73% of liquid alcohols, melting point 18.1° C and 27% of solid alcohols, melting point 44.4° C were obtained.

EXAMPLE 11 a. In corresponding manner as in Example 9, a continuous separation was carried out at 24.7° C, the aqueous solution containing 0.5% of Na decyl sulfate and 5% of $Na_2SO_4$. The aqueous fatty alcohol dispersion was separated in a solid-jacket centrifuge into liquid fatty alcohols on the one hand and an aqueous suspension of the solid fatty alcohols, on the other. Before melting, 12% of the aqueous phase without solid components were separated from the aqueous suspension of the solid fatty alcohols, and removed from the process cycle.

Thereby a smooth, continuous operation was made possible. The separated components of the aqueous phase removed from the process contained 0.05% of Na decyl sulfate. The residual dispersion of the solid fatty alcohols in the aqueous phase contained 0.53% of Na decyl sulfate.

The following products, 86% of liquid fatty alcohols, melting point 22.5° C and 14% of solid fatty alcohols, melting point 48.5° C were obtained.

b. With a procedure according to prior art it would have been necessary to discharge an aqueous solution with a wetting agent content of 0.5%. Since, in the procedure of the invention, the aqueous phase to be discharged contained only 0.05% of wetting agent, the wetting agent loss resulting from the discharge of a portion of the recycling solution was reduced to 1/10.

The preceding specific embodiments are illustrative of the practice of the invention. It is to be understood, however, that other procedures known to those skilled in the art may be employed without departing from the spirit of the invention or the scope of the appended claims.

We claim:

1. A continuous process for the separation of mixtures of fatty alcohols into fatty alcohol mixtures of different melting points by the steps of continuously dispersing said mixture of fatty alcohols consisting of an oily phase and a solid phase in a recycling aqueous wetting agent solution at a temperature whereby a dispersion of liquid fatty alcohol and solid fatty alcohol particles is obtained, continuously separating said dispersion into two phases of different specific gravities, a lighter phase consisting substantially of liquid fatty alcohol fractions and a heavier phase consisting substantially of solid fatty alcohol particles dispersed in said aqueous wetting agent solution, continuously withdrawing said liquid fatty alcohol fractions, continuously separating said solid fatty alcohol particles from 10% to 70% by weight of said aqueous wetting agent solution, continuously withdrawing said separated aqueous wetting agent solution, continuously melting said solid fatty alcohol particles with the remaining aqueous phase and adhering wetting agent, in an aqueous phase, continuously separating said melted fatty alcohol particles containing little wetting agent from an aqueous phase enriched with wetting agent, continuously withdrawing said melted fatty alcohol particle, continuously recycling said aqueous phase enriched with wetting agent to said dispersing step and continuously replacing said withdrawn part of said recycling aqueous wetting agent solution with a fresh aqueous solution whereby the concentration of said recycling aqueous wetting agent solution is maintained substantially constant at said dispersing step.

2. The process of claim 1 wherein the amount of said separated aqueous wetting agent solution withdrawn is such that said solid fatty alcohol particles are obtained in a concentrated aqueous suspension which is flowable.

3. The process of claim 1 wherein the amount of said separated aqueous wetting agent solution withdrawn is practically free of fatty alcohol particles and is from 15% to 50% by weight of said recycling aqueous wetting agent solution.

4. The process of claim 1 wherein said separated aqueous wetting agent solution withdrawn is approximately all that separated from said solid fatty alcohol particles and fresh aqueous phase is added to this separated solid fatty alcohol particles to form a flowable slurry.

5. The process of claim 1 wherein said solid fatty alcohol particles with the remaining aqueous phase and adhering wetting agent contain from 40% to 70% by weight of water.

6. The process of claim 4 wherein said solid fatty alcohol particles with the remaining aqueous phase and adhering wetting agent contain from 40% to 70% by weight of water.

7. The process of claim 1 wherein said mixture of fatty alcohols is a liquid fatty alcohol mixture previously separated by the process.

8. The process of claim 1 wherein said mixture of fatty alcohols is a solid fatty alcohol mixture previously separated by the process.

* * * * *